US00PP21294P2

(12) United States Plant Patent
van der Knaap

(10) Patent No.: US PP21,294 P2
(45) Date of Patent: Sep. 14, 2010

(54) *SPATHIPHYLLUM* PLANT NAMED 'SPARANKE'

(50) Latin Name: *Spathiphyllum Schott*
Varietal Denomination: Sparanke

(75) Inventor: Leonardus Johannus Maria van der Knaap, Naaldwijk (NL)

(73) Assignee: Knaap Licenties B.V., Naaldwijk (NL)

( * ) Notice: Subject to any disclaimer, the term of this patent is extended or adjusted under 35 U.S.C. 154(b) by 0 days.

(21) Appl. No.: 12/386,660

(22) Filed: Apr. 20, 2009

(51) Int. Cl.
*A01H 5/00* (2006.01)

(52) U.S. Cl. ..... Plt./364

(58) Field of Classification Search ..... Plt./364
See application file for complete search history.

*Primary Examiner*—Annette H Para
(74) *Attorney, Agent, or Firm*—C.A. Whealy

(57) ABSTRACT

A new and distinct cultivar of *Spathiphyllum* plant named 'Sparanke', characterized by its upright, outwardly arching and uniform plant habit; freely clumping growth habit; bushy and dense plants; large glossy dark green-colored leaves; freely flowering habit; white-colored spathes that are positioned above and beyond the foliage on strong and erect scapes; and good inflorescence longevity.

2 Drawing Sheets

Botanical designation: *Spathiphyllum Schott.*
Cultivar denomination: 'Sparanke'.

BACKGROUND OF THE INVENTION

The present invention relates to a new and distinct cultivar of *Spathiphyllum* plant, botanically known as *Spathiphyllum Schott*. and hereinafter referred to by the name 'Sparanke'.

The new *Spathiphyllum* plant is a product of a controlled breeding program conducted by the Inventor in Naaldwijk, The Netherlands. The objective of the breeding program is to create new year-round flowering *Spathiphyllum* cultivars that have glossy dark green-colored leaves, large white-colored spathes and good postproduction longevity.

The new *Spathiphyllum* plant originated from a cross-pollination made by the Inventor in November, 2004, in Naaldwijk, The Netherlands of a proprietary selection of *Spathiphyllum Schott*. identified as code number 20011048-01, not patented, as the female, or seed, parent with a proprietary selection of *Spathiphyllum Schott*. identified as code number 20050805-01, not patented, as the male, or pollen, parent. The new *Spathiphyllum* was discovered and selected by the Inventor as a single flowering plant within the progeny of the stated cross-pollination in a controlled greenhouse environment in Naaldwijk, The Netherlands in May, 2006.

Asexual reproduction of the new *Spathiphyllum* plant by tissue culture in a controlled environment in Maasdijk, The Netherlands since June, 2006 has shown that the unique features of this new *Spathiphyllum* are stable and reproduced true to type in successive generations of asexual reproduction.

SUMMARY OF THE INVENTION

Plants of the new *Spathiphyllum* have not been observed under all possible environmental conditions. The phenotype may vary somewhat with variations in environment such as temperature and light intensity, without, however, any variance in genotype.

The following traits have been repeatedly observed and are determined to be the unique characteristics of 'Sparanke'.

These characteristics in combination distinguish 'Sparanke' as a new and distinct cultivar of *Spathiphyllum:*

1. Upright, outwardly arching and uniform plant habit.
2. Freely clumping growth habit; bushy and dense plants.
3. Large glossy dark green-colored leaves.
4. Freely flowering habit.
5. White-colored spathes that are positioned above and beyond the foliage on strong and erect scapes.
6. Good inflorescence longevity.

Plants of the new *Spathiphyllum* differ from plants of the female parent selection in the following characteristics:

1. Plants of the new *Spathiphyllum* have smaller leaves than plants of the female parent selection.
2. Plants of the new *Spathiphyllum* have glossier leaves than plants of the female parent selection.
3. Plants of the new *Spathiphyllum* have smaller spathes than plants of the female parent selection.

Plants of the new *Spathiphyllum* differ from plants of the male parent selection in the following characteristics:

1. Plants of the new *Spathiphyllum* have darker green-colored leaves than plants of the male parent selection.
2. Plants of the new *Spathiphyllum* have glossier leaves than plants of the male parent selection.
3. Plants of the new *Spathiphyllum* have smaller spathes than plants of the male parent selection.

Plants of the new *Spathiphyllum* can also be compared to plants of *Spathiphyllum* spp. 'Sparego', disclosed in U.S. Plant Pat. No. 11,457. In side-by-side comparisons conducted in Naaldwijk, The Netherlands, plants of the new *Spathiphyllum* differed from plants of 'Sparego' in the following characteristics:

1. Plants of the new *Spathiphyllum* were more freely branching than plants of 'Sparego'.
2. Plants of the new *Spathiphyllum* had smaller spathes than plants of 'Sparego'.
3. Spathes of plants of the new *Spathiphyllum* were whiter in color than spathes of plants of 'Sparego'.

BRIEF DESCRIPTION OF THE PHOTOGRAPHS

The accompanying photographs illustrate the overall appearance of the new *Spathiphyllum*. These photographs show the colors as true as it is reasonably possible to obtain in colored reproductions of this type. Colors in the photographs may differ slightly from the color values cited in the detailed botanical description which accurately describe the colors of the new *Spathiphyllum*.

The photograph on the first sheet is a side perspective view of a typical plant of 'Sparanke' grown in a container.

The photograph on the second sheet is a close-up view of a typical inflorescence of 'Sparanke'.

DETAILED BOTANICAL DESCRIPTION

The aforementioned photographs and following observations and measurements describe plants grown in 17-cm containers in Naaldwijk, The Netherlands during the winter in a glass-covered greenhouse. Plants were grown under conditions and practices which approximate those generally used in commercial *Spathiphyllum* production. During the production of the plants, day temperatures ranged from about 19° C. to 24° C., night temperatures ranged from about 19° C. to 22° C. and light levels were about 5,000 lux. Plants were 36 weeks old when the photographs and the detailed description were taken. In the following description, color references are made to The Royal Horticultural Society Colour Chart, 2001 Edition, except where general terms of ordinary dictionary significance are used.

Botanical classification: *Spathiphyllum Schott*. 'Sparanke'.

Parentage:

*Female, or seed, parent.*—Proprietary selection of *Spathiphyllum Schott*. identified as code number 20011048-01, not patented.

*Male, or pollen, parent.*—Proprietary selection of *Spathiphyllum Schott*. identified as code number 20050805-01, not patented.

Propagation:

*Type.*—By tissue culture.

*Time to initiate roots.*—About eleven days at 23° C.

*Time to produce a rooted young plant.*—About 215 to 240 days at 21° C.

*Root description.*—Medium in thickness, fibrous; white in color.

*Rooting habit.*—Moderately branching, moderately dense.

Plant description:

*Plant shape.*—Upright and outwardly arching plant habit, uniform inverted triangular habit.

*Growth habit.*—Freely clumping, bushy and dense growth habit; about 15 clumps per plant; moderately vigorous growth habit.

*Plant height, from soil level to top of leaf plane.*—About 52.5 cm.

*Plant height, from soil level to top of inflorescences.*—About 61.8 cm.

*Plant diameter or spread.*—About 57.5 cm.

*Foliage description.*—Arrangement: Alternate; simple. Length: About 26.9 cm. Width: About 9.8 cm. Shape: Narrowly ovate to narrowly elliptic. Apex: Narrowly apiculate. Base: Attenuate. Margin: Entire; slightly undulate. Texture, upper and lower surfaces: Smooth, glabrous; slightly leathery. Luster, upper and lower surfaces: Glossy. Venation pattern: Pinnate. Color: Developing leaves, upper surface: Close to 143A and 143B. Developing leaves, lower surface: Close to 137D. Fully expanded leaves, upper surface: Slightly darker than between 137A and 139A; venation, close to 144A. Fully expanded leaves, lower surface: Close to 137C to 137D; venation, close to 145A to 145B. Petiole: Length (excluding geniculum): About 16.9 cm. Diameter, just below geniculum: About 5 mm. Diameter, at plant base: About 8 mm. Texture, upper and lower surfaces: Smooth, glabrous; slightly glossy. Color, upper and lower surfaces: Close to 143A. Geniculum length: About 3.6 cm. Geniculum diameter: About 6 mm. Geniculum texture: Smooth, glabrous; slightly glossy. Geniculum color, upper and lower surfaces: Close to 146B. Wing length: About 14.7 cm. Wing diameter: About 9 mm. Wing color: Close to 143A; towards the base, close to 143B.

Inflorescence description:

*Inflorescence arrangement/habit.*—Slightly cupped erect spathes with columnar spadices held above and beyond the foliage on strong and erect scapes. Flowering structures arise from leaf axils. Freely and continuous flowering year-round in The Netherlands; typically about 14 inflorescences develop per plant.

*Fragrance*—Faintly to moderately fragrant; sweet and pleasant. Inflorescence longevity: Inflorescences last about three weeks on the plant; inflorescences persistent.

*Spathe.*—Length: About 14.3 cm. Width: About 6.6 cm. Depth: About 2.8 cm. Shape: Elliptic to broadly elliptic. Apex: Apiculate; twisting. Base: Obtuse. Margin: Entire. Texture, upper and lower surfaces: Smooth, glabrous; slightly leathery. Luster, upper and lower surfaces: Glossy. Color: When developing, front surface: Close to N155B; at the apex, close to 145B to 145D. When developing, rear surface: Close to N155B; at the apex, close to 145A. Fully developed, front surface: Close to N155B; at the apex, close to 145D; with development, color becoming closer to 144B. Fully developed, rear surface: Close to N155B; at the apex, close to 145A; with development, color becoming closer to 144B.

*Spadix.*—Length: About 5.4 cm. Diameter: About 1.3 cm. Shape: Columnar, tapering towards the apex; apex, obtuse; base, obtuse; cross-section, rounded. Aspect: Mostly erect. Color: Immature: Close to 158C. Mature: Close to 158B to 158C. Flowers: Quantity per spadix: Numerous, about 180. Shape: Rounded. Height: About 3 mm. Diameter: About 3.5 mm. Anther color: Close to 158B to 158C. Pollen amount: Scarce. Pollen color: Close to 155D. Stigma shape: Ovoid. Stigma color: Close to N155B. Ovary color: Close to 158B.

*Scape.*—Length: About 40.4 cm. Diameter: About 4.5 mm. Strength: Strong. Aspect: Erect to about 15° from vertical. Color: Close to 144A; towards the base, close to 144C to 144D.

*Seed and fruit.*—Seed and fruit development has not been observed on plants of the new *Spathiphyllum*.

Disease/pest resistance: Plants of the new *Spathiphyllum* have not been observed to be resistant to pathogens or pests common to *Spathiphyllum*.

Temperature tolerance: Plants of the new *Spathiphyllum* have been observed to be tolerant to temperatures ranging from about 15° C. to about 36° C.

It is claimed:

1. A new and distinct *Spathiphyllum* plant named 'Sparanke' as illustrated and described.

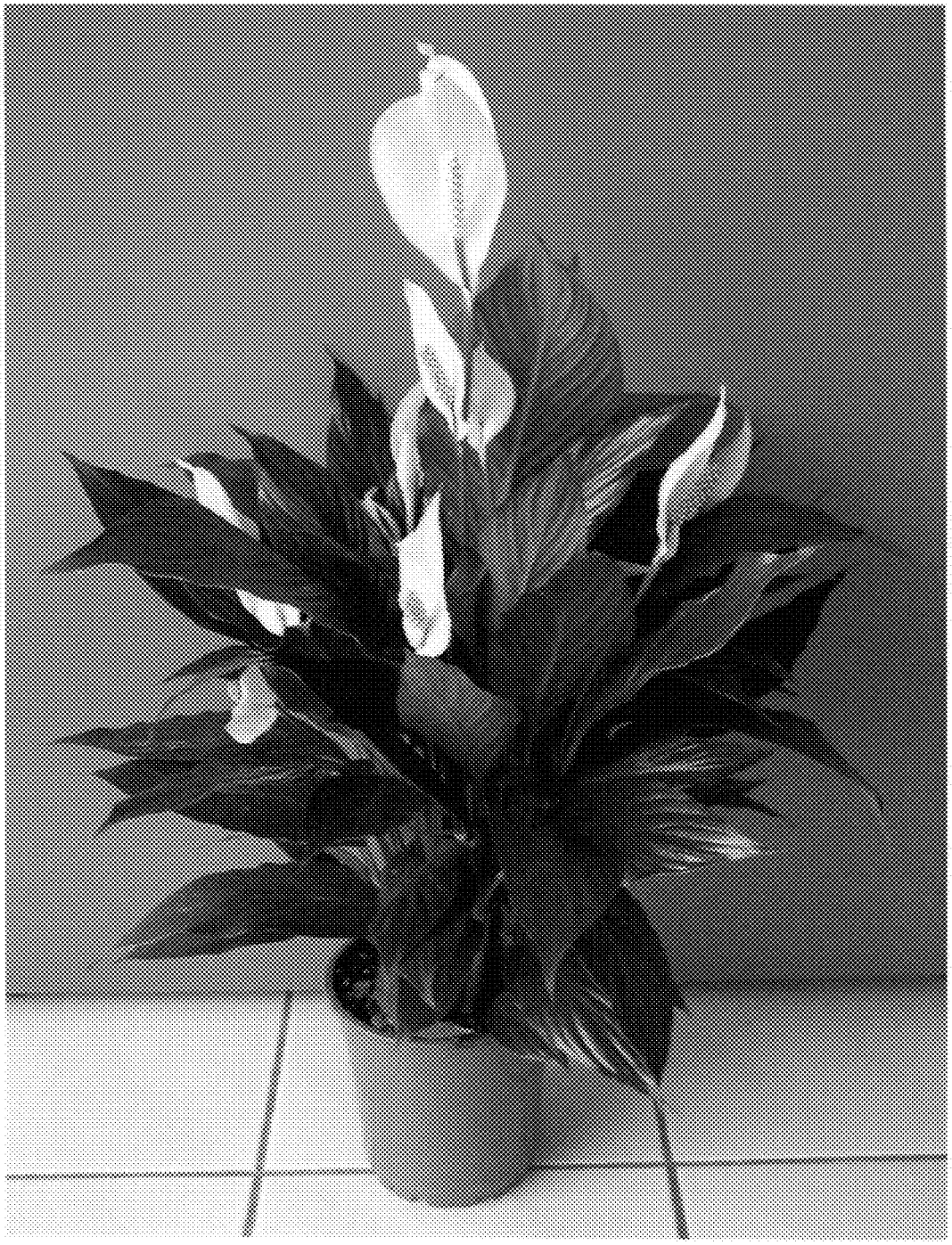

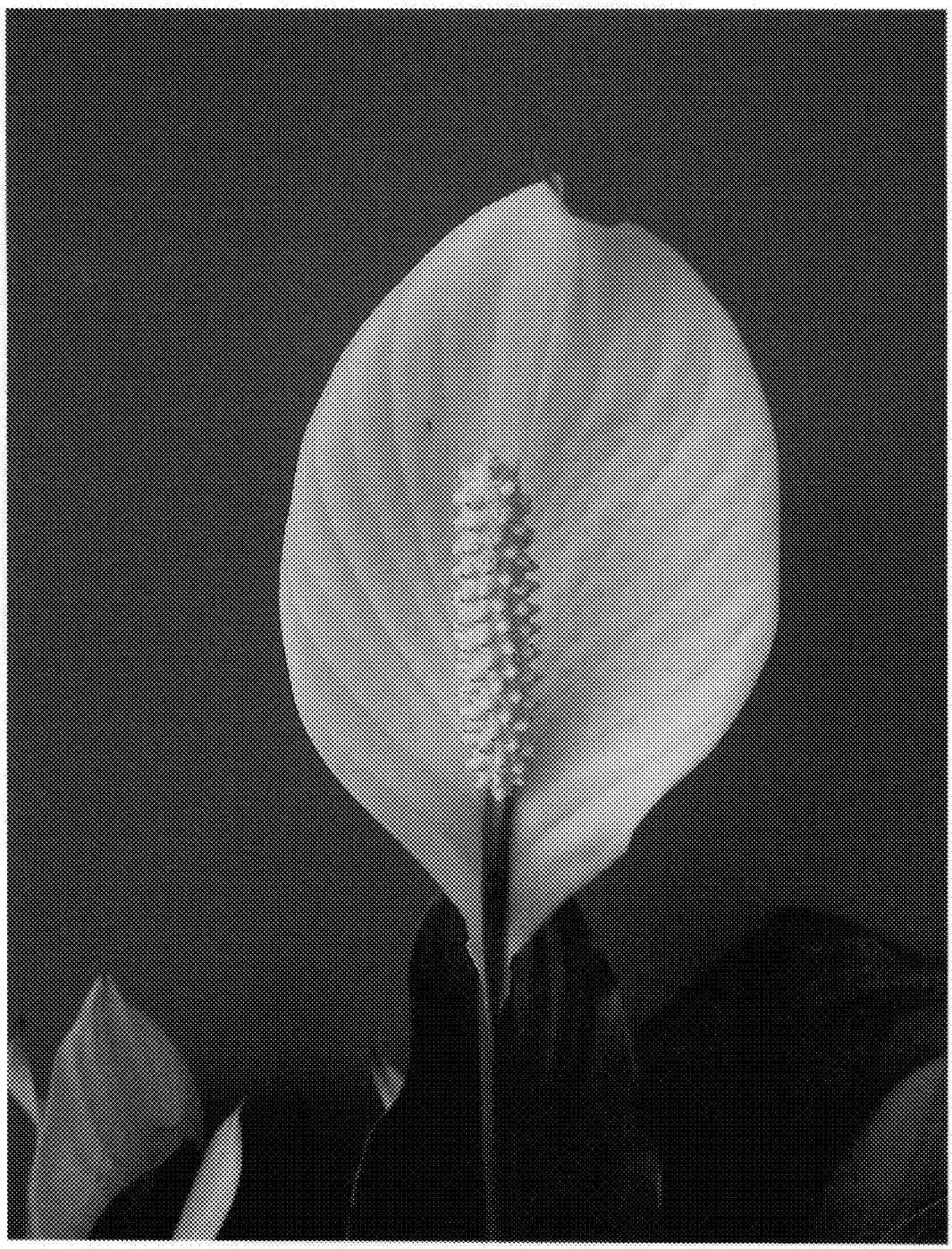

* * * * *